APPARATUS AND METHOD FOR PREVENTING BLOOD CLOTTING

Original Filed Dec. 12, 1966 2 Sheets-Sheet 1

INVENTOR
ITZHAK E. BENTOV
BY
Wolff, Greenfield & Hieken

APPARATUS AND METHOD FOR PREVENTING BLOOD CLOTTING

Original Filed Dec. 12, 1966 2 Sheets-Sheet 2

INVENTOR
ITZHAK E. BENTOV
BY
Wolf, Greenfield & Hieken

United States Patent Office

Re. 27,923
Reissued Feb. 19, 1974

27,923

APPARATUS AND METHOD FOR PREVENTING BLOOD CLOTTING

Itzhak E. Bentov, 241 Glezen Lane,
Wayland, Mass. 01778

Original No. 3,491,756, dated Jan. 27, 1970, Ser. No. 604,523, Dec. 12, 1968, which is a continuation-in-part of abandoned application Ser. No. 547,479, May 4, 1966. Application for reissue Dec. 23, 1971, Ser. No. 211,531

Int. Cl. A61m *5/32*

U.S. Cl. 128—221 14 Claims

Matter enclosed in heavy brackets [ ] appears in the original patent but forms no part of this reissue specification; matter printed in italics indicates the additions made by reissue.

ABSTRACT OF THE DISCLOSURE

A means for preventing blood clots and the like which are occasioned by leaving a medical device such as a catheter or needle in a body for long periods of time in the form of a flexible or rigid obturator comprising a metal (aluminum, magnesium, etc.) high in the electrochemical series, containing wire or probe which fits into a needle or cathether and generates a negative voltage and produces a soft gel to inhibit clot formation. An electrochemical arrangement and a circuit provide means for establishing a selected voltage within the tissue which prevents clot formation and also generates a gel. Also provided is a method for minimizing coagulation of blood about a medical device partially inserted into a medically formed opening in body tissue. *A hollow tubular needle* [means] *is formed with a surface which prevents blockage by blood in the body.*

*RELATED APPLICATIONS*

*This invention is a reissue application of Pat. No. 3,491,756 issued Jan. 27, 1970 which in turn is a continuation-in-part of application Ser. No. 547,479 filed May 4, 1966, and now abandoned.*

[The present invention is a continuation-in-part of application Ser. No. 547,479, filed May 4, 1966, and now abandoned.]

The present invention relates to blood clotting and more particularly to a means and method for preventing obstruction of surgical appliances which have passageways that carry blood within such passageways. For example, hypodermic needles used for withdrawing blood from the arterial or venous system of the body are often clogged by blood clots if left in the body over a prolonged period of time.

Blood clotting in narrow passages of surgical appliances has long been a problem. Particularly when blood is to be drawn from an individual at periodic intervals over time spans of eight or more hours, difficulties have been encountered. Frequently, it is necessary to repeatedly introduce conventional hypodermic needles into the venous or arterial system at the preselected time periods in order to draw blood samples. If a hypodermic needle of a conventional type is introduced into the blood vessels and left in the body while not used for passage of fluids between the preselected times, clotting of blood within the needle shaft and outside of it at the tip obstructs the passageway. It has been unsatisfactory to introduce a hypodermic needle and use it as a tap at preselected times in an individual for that reason. For the same reason, hypodermic needles cannot be left in the body and used to introduce medicants at preselected time intervals since it is found that the needle is obstructed in relatively short times if this is done. Thus, a patient must often be subjected to repeated needle punctures in many medical procedures.

It is known that blood clotting occurs by a series of involved chemical reactions which start as soon as the blood comes into contact with damaged tissue or some foreign surface such as a conventional stainless steel hypodermic needle. Soluble protein, i.e., fibrinogen, is changed into an insoluble protein form known as fibrin. The fibrin precipitates in the blood and first forms a thrombus which later becames hard and tough after which a serum is forced out of the clot. Thus, the clot which normally obstructs conventional stainless steel hypodermic needles is a protein mass which often forms several minutes after blood remains stagnant in a shaft passageway of a hypodermic needle or forms surrounding the needle tip.

An important feature of this invention is to provide a means for use in contact with blood which prevents obstruction of a blood passageway by clotting over long periods of time.

Another object of this invention is to provide a means in accordance with the preceding object which is inexpensive and is particularly adapted for use in hypodermic needles which can be introduced into an individual and left therein as a top or inlet passageway to the blood system over long periods of time.

Still another object of this invention is to provide a means in accordance with the preceding object which substantially reduces the discomfort to an individual normally encountered when a hypodermic needle is subcutaneously introduced into a blood vessel.

Still another object of this invention is to provide a means in accordance with the preceding objects which can be used with conventional surgical appliances such as catheters, hypodermic syringes, blood transfusion bottles, scalp vein needles and the like, as well as in a variety of medical procedures such as multiple drug infusions, interrupted IV drippings, and multiple blood tests such as a glucose tolerance test.

Still another object of this invention is to provide a method for preventing obstruction of hypodermic needles, blood conduits or other surgical devices which have passageways exposed to blood.

In the present invention there is provided a means for generating a negative potential at the locus of a foreign body which is exposed to blood. Preferably associated with this negative potential is a means for generating a clot inhibiting material at the locus of the foreign body. This may comprise a gel which presumably comprises an oxidized product, preferably a combination of magnesium and aluminum hydroxide. In an alternate embodiment the clot inhibiting material may comprise an alkaline producing emulsifying-like material; if we consider the blood as an emulsion.

In the preferred embodiment of the invention, the means for generating a negative potential comprises an aluminum alloy member. This member is arranged to become a source of negative potential when it comes into contact with blood and tissue. Over a period of time a clot inhibiting material forms about the member. This takes the form of a gel. It is believed this gel comprises an oxide which subsequently hydrolizes into a hydroxide. The gel interferes with the formation of clots, acts as a relaxant or local anesthetic, acts as an emulsifier to stabilize the blood and inhibits bacterial growth.

The invention may have a number of specific applications. For example, it may be used to prevent clotting in a hypodermic needle which is left in the blood. In this preferred embodiment the needle is preferably formed of stainless steel and an aluminum alloy obturator is introduced into the needle with the end of the obturator projecting through the needle when the needle is not in use. The aluminum alloy obturator develops a negative charge in the order of magnitude of —.7 to —.85 volt with respect to tissue. The charge tends to repel negatively charged blood cells and platelets, thereby interfering with normal clotting. A gel of the type described above is also formed to function as indicated.

In another specific embodiment, a hypodermic needle having a hollow shaft comprises a metal such as aluminum. The aluminum forms an oxide at the surface of the needle shaft which oxide in turn forms a hydroxide on exposure to water or blood. The oxidized product forms as a gel on the surface of the needle when exposed to the blood, and the gel prevents obstruction. Preferably, the needle is composed of a combination of at least two metals such as aluminum and magnesium where the magnesium is more reactive than the aluminum and forms magnesium hydroxide. The magnesium hydroxide has a high pH in the alkaline range which provides for some degree of self-sterilization of the needle and has a proteolytic action tending to emulsify blood rather than permit buildup of clots within the needle shaft or in its vicinity. The corrosion mechanism of both aluminum and magnesium will leave the needle negatively charged with respect to the body, and the negative charge aids in repelling blood particles from the vicinity of the needle.

The means of the present invention can be used by superimposing a negative charge on a needle. When a hypodermic needle made of any metal exposed to blood is negatively charged, the walls of the needle shaft repel normally negatively charged blood particles preventing clot formation adjacent the inner and outer walls.

The present invention also contemplates an improved obturator of flexible design which is especially useful in connection with catheters that extend into the body and require a great deal of flexing.

"Foreign element" as defined herein means a conduit such as a needle or catheter adapted to be partially contained in a body for the purpose of flowing blood to or form the body or other fluids to or from blood vessels. "Physiologically non-toxic" or "substantially physiologically non-toxic" as used herein in connection with the described or claimed components or material is intended to indicate such components or material are [intended to indicate such components or material are] non-toxic to the tissue to which they are exposed in the quantity or volume and for the time periods normally involved in connection with apparatus of the type described.

The present invention provides a means for preventing formation of blood clots about a foreign element such as a hypodermic needle or catheter inserted in and maintained partially within a body and in contact with tissue. This means includes a non organic, physiological non-toxic member positioned immediately adjacent the foreign element and at least partially projecting into the body, the non organic member having means for producing a negative voltage with respect to said body tissue, and preferably means for producing an alkaline corrosion product in the form of a soft gel.

These and other objects, features and advantages of the present invention will be better understood from the following specification when read in conjunction with the accompanying drawings in which.

Figure 5:
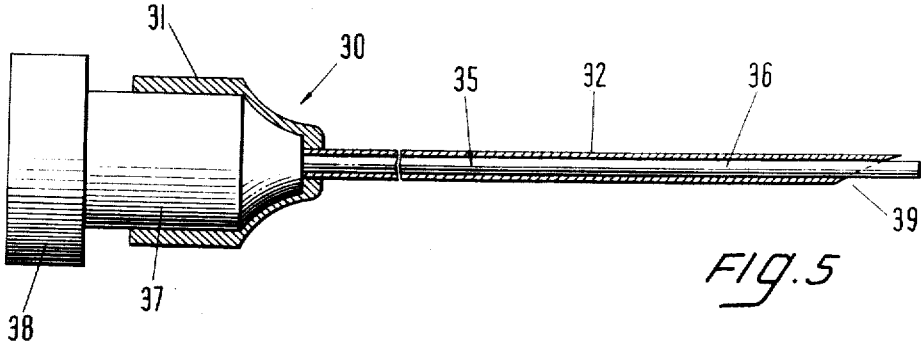
FIG. 5 is a cross-sectional elevation of the preferred form of the present invention.

Referring first to the preferred embodiment of the invention as illustrated in FIG. 5, there is shown a conventional hypodermic needle 30 having a conventional hub 31 and hollow pointed shaft 32 integrally connected to the hub 31. The needle is preferably made of stainless steel of the type conventionally used for these hypodermic needles and with the tip sharpened in a conventional fashion. This needle may be conventionally used. If the needle 30 is allowed to remain in a patient's blood vessel, blood will clot at the needle tip or in the needle. Such clotting may be avoided by the introduction into the needle of an obturator 35. This obturator 35 comprises an elongated member 36 rigidly secured to a handle or head 37. The elongated member 36 has a diameter slightly less than the diameter of the opening through the needle shaft so that it can slide through the opening in a relatively snug fit. The head 37 is shaped to conform with the opening in the hub 21 of the needle, and may be provided with a finger grip 38 adapted to be used by an operator for insertion and removal of the obturator 35. The elongated member 36 is preferably formed of an aluminum-magnesium alloy. This aluminum-magnesium alloy member 36 will have a naturally formed thin oxide layer or coating on its surface which insulates it from the inner wall of the needle shaft 32. When the obturator 35 is inserted in a needle 30 in body tissue, an electrical circuit is formed in which the aluminum-magnesium alloy member 36 has a negative potential. The member 36 is electrically connected to the needle shaft 32 through the oxide layer which functions as a series of low resistors. A higher resistance is formed between the projecting portion of the obturator 35 and the body tissue of the patient in whose body the needle and obturator is inserted. It has been found that the needle and obturator develop a negative potential with respect to the tissue in an order of magnitude of approximately —.7 volt to —.85 volt. This negative charge appears to repel the negatively charged blood cells and platlets thus interfering with normal clotting mechanisms around the needle and obturator. In addition the EMF of the circuit which is formed by this obturator and needle arrangement in the body oxidizes the surface of the alloy projecting into and in contact with the tissues. This oxide apparently hydrolizes to form a hydroxide. This hydroxide comprises a gel of aluminum and magnesium hydroxide. Since the preferable alloy utilized contains a predominance of aluminum, the hydroxide formed is predominantly aluminum. The mixture of aluminum and magnesium to form the alloy is preferably about 4½ percent magnesium and the balance aluminum. However, this composition may vary depending upon the desired results. The more magnesium included in the aluminum, the greater will be the production of hydrogen as a by-product during the formation of the aluminum and magnesium and aluminum hydroxide gel. In addition, the obturator becomes more brittle with the addition of more magnesium. On the other hand the more magnesium in the alloy, the more effective is the obturator in preventing clotting. Thus large amounts of magnesium in the magnesium-aluminum alloy or mixture should be used consistent and limited, however, by the body tolerance to the generation of hydrogen by the magnesium component. In this connection, experiments have shown that pure aluminum with about 1% magnesium did not work as well as aluminum with about 2.5% magnesium of the total alloy or mix, and pure aluminum with about 5% magnesium of the total alloy or mix appeared to yield even better results. By extrapolation it would appear that an alloy or mix of aluminum and magnesium with up to 20% magnesium by weight would be the upper limit at which too much gassing would limit further increases of magnesium.

The hydroxide formed by the aluminum and magnesium alloy is a soft gel that ordinarily surrounds the tip of the obturator and the needle. It has been found that this gel interferes with the formation of clots in the vicinity of the needle and obturator tip. In addition, the magnesium hydroxide component of the gel is known to have a blocking effect on sensory nerves; consequently, it acts as a relaxant and is a local anesthetic for the general area of the puncture rendering the area less painful and counteracting the inflammatory effects which a stainless steel needle has on tissue. The hydroxide environment produced by the aluminum magnesium hydroxide also tends to act as an emulsifier which stabilizes the blood as an emulsion, thus also interfering with clotting. Finally, the surface alkalinity of the metal acts to inhibit the growth of bacteria and with a sufficiently high magnesium content, it makes the area bactericidal or self-sterilizing. Of these mechanisms, the most important one is the negative charge of the alloy member 36.

It has been found that whether or not needle shaft 32 and/or the obturator has an oxide coating is irrelevant with respect to establishing a negative voltage on the needle and obturator with respect to the tissue. It has also been found that by making the obturator of an alloy, such as an aluminum-magnesium alloy, and the needle of a stainless steel, there is no clotting of blood platelets in the opening between the needle and the obturator as occasionally would be the case if such an alloy needle were used with a stainless steel obturator.

Although an aluminum magnesium alloy obturator used in conjunction with a stainless steel needle as described in connection with the FIG. 5 is a preferred embodiment, other metals or combinations may also be used. There are, however, certain requirements for the obturator or other clot-repelling devices which limit and define the scope of the invention. First, the metal of the obturator or its reaction products with living tissue should be physiologically non-toxic in quantities used in the performance of their function. Second, the obturator or clot repelling device should be formed of a metal that produces a negative charge with respect to tissue when in contact with it. Thus, if an alloy or non alloy composition is used, it should contain a metal high in the electrochemical series as defined by the Handbook of Chemistry and Physics, (Chemical Rubber Publishing Company), 43rd ed., page 1740, Oxidation Potentials of Elements, and should be no lower than thallium or above as listed. These metals may be utilized as active elements functioning to generate a negative charge relative to and when in contact with body tissues. Elements however, being lower in the electromotive series, may be used as a matrix of inert materials with respect to the active materials identified within the group described above. Thus, for example, preferred metals consist of aluminum, magnesium, titanium, lithium, sodium, potassium, rubidium, calcium and strontium. These metals produce high negative potentials with respect to tissues and also yield strongly alkaline reaction products. They may be mixed or alloyed with the noble metals of higher atomic weights to produce desired results.

Third, it is desirable that the corrosion products of the metals described above be slightly alkaline to act as emulsifying agents and stabilizers for blood emulsion.

Fourth, it is desirable that the corrosion products form a soft gel which excludes the formation of a clot at the tip of a needle or in the vicinity of the metal.

Fifth, it is desirable that the reaction products have a local depressant action on nerve endings.

Sixth, the metals should have a mechanical strength and flexibility suitable for the particular application.

The metals described above may, within certain limits, be used in their pure form. These limits, for example, include the first requirement mentioned above, which would severely limit the extent to which the magnesium may be used in its pure form, because pure magnesium would rapidly build up gases in the body and would therefore have to be withdrawn after a relatively short time. Gasing due to magnesium, however, may be minimized by alloying it or mixing it with aluminum, as described above, so that the magnesium comprises no more than 50 percent of the total weight of the obturator.

The obturator or repelling device may also be formed of an alloy of a relatively inert matrix metal such as a metal having an atomic number of over 50, which metal supplies mechanical strength to the obturator. The alloy would also incorporate one of the active metals referred to above as an additive which would produce an electrical negative charge and the desired chemical reaction. In place of an alloy, a mixture of a matrix metal and an active metal of the types described above may also be used.

A combination of several metals where two metals interact with each other to yield a desired reaction product, may also be used. In this case, only one metal acts as a cathode and the other as an anode.

A combination of powdered metals incorporated into a plastic matrix for flexibility is also contemplated. The plastic material would preferably be inert and the powdered metal would comprise one of the active metals referred to above having an atomic number of less than 50. The reaction products of two metals such as oxides or hydroxides of metals, or both, may be incorporated into an inert plastic matrix to produce emulsifying anesthetic actions of the type described herein.

This invention also contemplates an arrangement in which a conventional style of stainless steel needle is coated on its inner and/or outer surface with a film of material of the type described above to a thickness of up to several thousandths of an inch. Preferably, such a coating would comprise aluminum or the aluminum magnesium alloy described above. This coated needle could then be used with or without an obturator of the types herein described. It has been found that an aluminum-magnesium alloy coated needle is signficantly less irritating in many venous applications.

Also contemplated by this invention is an obturator formed of a plastic matrix having a substantial quantity of finely divided aluminum and magnesium hydroxide. This obturator will yield small amounts of negative ions that will render an area immediately adjacent the obturator alkaline and thereby inhibit clot production. Contemplated in this obturator is a mix of an inert plastic such as polypropylene PVC or polyethylene in an amount by weight of up to 25 percent with a balance by weight of aluminum hydroxide and magnesium hydroxide. Preferably, equal amounts should be used, but any relevant ratio of aluminum to magnesium hydroxide including all of one or the other may be used. Although smaller amounts of plastic may be used in combination with the metal, a range of about up to 50 percent plastic with 50 percent metal hydroxide by weight has been found to be satisfactory. Other mixes of metal or metal hydroxides may be used provided they comply with the requirements referred to above.

Figure 6:
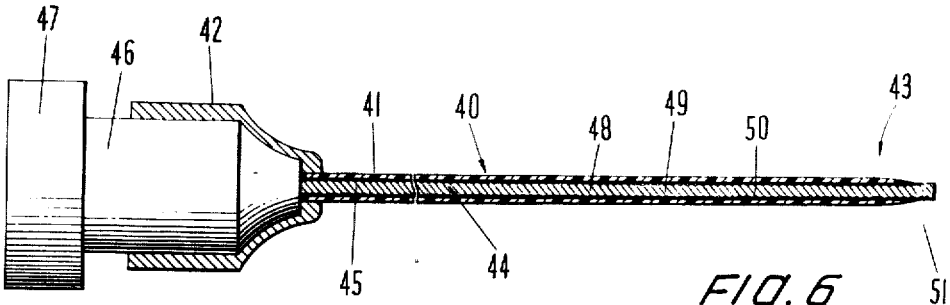
FIG. 6 is a cross-sectional view of an alternate embodiment of the invention used in connection with a catheter.

A modification of the invention is illustrated in FIG. 6. In this arrangement, there is provided a short catheter 40. This short catheter comprises a tubular member 41 permanently connected to a hub 42. The eubular member 41 is normally made of a flexible plastic, such as polypropylene, and is introduced as a short catheter into the patient's vein or other appropriate place by a needle which fits snugly through the tubular member 41. The member is introduced into the vein and is then withdrawn leaving the tubular member 41 with its forward end 43 inside the vein. Because of the flexibility of the plastic, the patient may flex the catheter as desired. Because this type of short catheter is ordinarily subject to moving and flexing, it is important to provide an obturator 44 which is also flexible. The obturator 44 comprises a shaft 45 and head 46. The head 46 fits into the hub 42 and may be provided with a finger grip 47. The shaft 45 of the obturator is composed of a plurality of lengths of wire 48, 49 and 50, twisted into a cable. These wires may comprise two aluminum alloy wires of a material of the type previously described, together with a stainless steel wire. Alternatively, if desired, the wires may all be formed of an aluminum alloy of the type previously described. However, the combination of aluminum and alloy and stainless steel wires is preferred in order to provide a higher voltage potential. These wires 48, 49 and 50 are loosely twisted together to provide a flexible shaft for the obturator. In addition, the loose twisting provides openings between which body fluids may pass in that portion of the wires projecting from the catheter into the body tissues. This permits a greater surface area at the exposed tip 51 of the obturator. The exposed tip 51 with its open wires allows formation of a greater amount of gel of the type previously described. In the absence of an obturator of this type with a catheter formed of plastic material, blood will clot in the catheter as soon as feeding through the catheter is stopped. The catheter of the type described in FIG. 6 may, however, be left in the patient's body without the formation of clots for prolonged periods of time.

In an alternate embodiment of the invention a hypodermic needle such as indicated at 10 is of conventional configuration having a conventional hub 11 adapted to be connected to a conventional hypodermic syringe as by a force fit of the hub on the barrel of the syringe. A needle shaft 12 is connected with the hub having a conventional beveled sharpened tip or point 13. While such needles are usually made of stainless steel, in this embodiment the needle is made entirely of an alloy of primarily aluminum and magnesium known as a 5052 alloy having a composition listed as follows with all percentages being by weight of the entire composition:

| | Percent |
|---|---|
| Silicon and iron | .45 |
| Copper | .1 |
| Manganese | .1 |
| Magnesium | 2.5 |
| Chromium | .15–.35 |
| Zinc | .1 |
| Inert impurities | .15 |
| Remainder aluminum. | |

The specific needle 10 of this embodiment is a nineteen gauge needle having a two inch shaft 12.

In a first example showing use of the needle 10 it was injected into an arm vein of an adult, male human and taped in place. Blood was withdrawn by use of a hypodermic syringe immediately after injection of the needle. The syringe was then disconnected from the needle and a polypropylene obturator 28 forced into the hub 11 to close the shaft opening at the junction of the hub and the shaft 12 and to extend adjacent of the tip of the needle snugly fitting within the shaft 12. The shaft of the obturator is preferably only slightly smaller in diameter than the diameter of the needle shaft 12 to permit a snug sliding fit. The obturator can be made of other materials than polypropylene including other plastics. The needle was left in the vein as a tap and no blood was withdrawn after the first withdrawn for a one hour period. The obturator was then withdrawn, another hypodermic syringe attached and 5 cc. of blood drawn. The obturator was then replaced. This procedure was repeated over a seven-hour period with no clogging of the needle 10 caused by blood clotting. Blood flowed freely through the needle during this time period at any point at which the tap was opened by withdrawing the obturator. When a conventional stainless steel needle of the same size and configuration was employed in the same experiment, clogging of the needle shaft at its inner wall occurred shortly after the obturator was positioned after the first withdrawal of blood and the needle was obstructed when an attempt was made to draw a blood sample through the needle.

Figure 2:
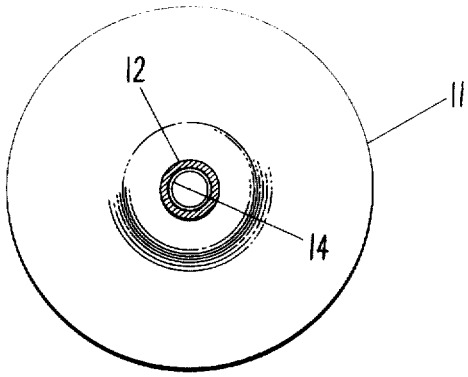
FIG. 2 is a cross-sectional view thereof through line 2—2 of FIG. 1.

It was found that the needle 10 formed an oxide coating over its exposed surfaces including its inner wall surface for the length of the shaft 12 and on the outer surface of the shat 12 positioned in the vein. This coating indicated at 14 when exposed to saline or blood, changes to a hydroxide and forms a gel easily seen under a 40× microscope in FIG. 2. This gel is assumed to be the same type of gel formed in the preferred embodiment and comprises a mixture of aluminum and magnesium oxides and hydroxides. These hydroxides appear to sterilize the surface of the needle to some extent and prevents blood from obstructing the passageway through the needle. It also appears to emulsify blood and dissolve any clot that tends to form. In addition, during the usage of the needle in the individual, as described in this first example, it was noted that the sensation and trauma to the patient was much less than when using a stainless steel needle since magnesium ions present at the surface of the wall adjacent the blood passageway of the shaft and on the outside of the needle, tend to anesthetize the nervous system at nerve synapses surrounding the needle so that little or no pain is experienced.

When the needle 10 is formed of substantially pure aluminum, advantageous results are obtained as with the aluminum-magnesium alloy although the anesthetic effect is not as noticeable.

While the preferred metal composition of the shaft 12 is preferably an aluminum-magnesium alloy, other metals alone or in combination can also be used to achieve desirable results in preventing obstruction of hypodermic needle shafts and other passageways for carrying blood. As pointed out above, substantially pure aluminum can be used or another metal material can be used as a base metal having alloyed therewith a material which is higher in the electromotive series than the base metal. Metals such as lithium, potassium, sodium, calcium, magnesium and aluminum are preferred for alloying with each other and with other metals lower in the electromotive series than themselves and form the desired coating such as 14. The percentage of each metal in any alloy used can vary greatly so long as the desired obstruction resistant coating is formed. For example, the magnesium content of the aluminum-magnesium alloy can be above 50% by weight. In all cases, these coatings impart an alkalinity to the localized area immediately adjacent the shaft which is believed to be responsible for prevention of obstruction of the shaft by blood clotting. The high pH has a proteolytic action which tends to dissolve any clots that may form. Preferably the pH at the wall surface exposed to the blood is above a pH of 8. In some cases metal particles or their oxides and hydroxides can be embedded at the surface of substantially rigid plastic walls or needle shafts to achieve the desired results. Thus, metal compositions of this invention such as magnesium, aluminum or their oxides and hydroxides in particle form can be mixed with thermoplastic or thermosetting materials and formed into hypodermic needle shafts.

In addition to the formation of oxidation products on the inner surface of the needle, the use of a metal alloy with one metal of the alloy higher in the electromotive series than the base metal is believed to set up local currents in the metal of the shaft which electrically repel blood particles and can aid in the prevention of obstruction by producing more gel.

Figure 1:
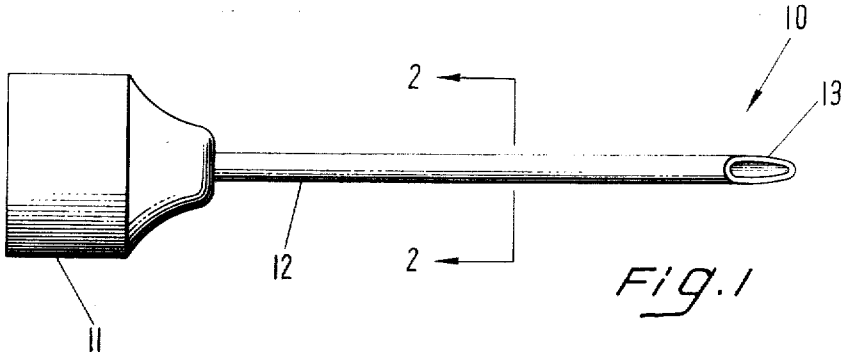
FIG. 1 is a side view of a hypodermic needle used in the present invention.
Figure 3:
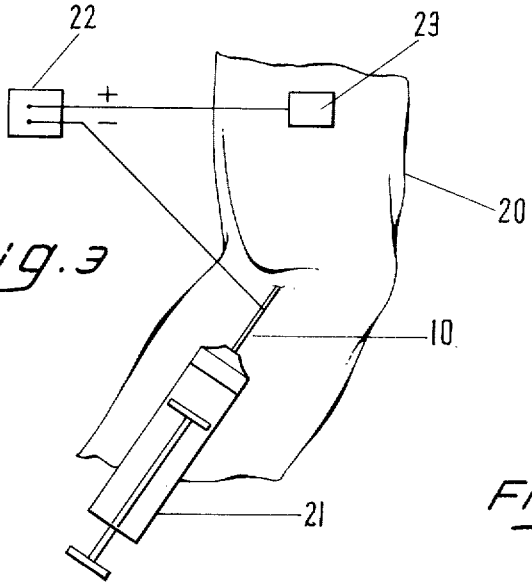
FIG. 3 is a semi-diagrammatic representation of a step in the method of this invention.
Figure 4:
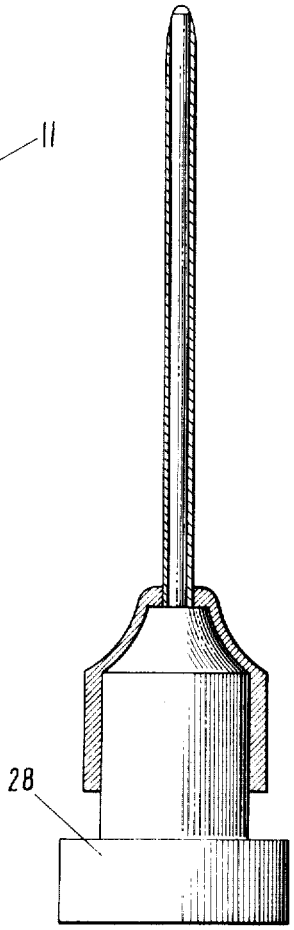
FIG. 4 is a cross-sectional elevation of an obturator of the present invention illustrating both a preferred embodiment and a modification of the invention.

In an alternate embodiment of the invention illustrated at FIG. 3, a stainless steel needle such as 10 is introduced into an arm vein of a human represented diagrammatically at 20. A syringe indicated at 21 is attached to the needle and blood withdrawn from the vein which is punctured by the needle 10. The needle 10 is then closed with an obturator as previously described in connection with FIG. 1 with the end of the obturator 28 projecting to the tip of the needle. The needle 10 is taped in place on the arm, and an electric current source indicated at 22 has its negative lead electrically connected to the needle shaft as by an alligator clip. The positive lead from the current source 22 is electrically connected with the arm through a lead attached to a conventional cardiogram electrode 23 with an underlying layer of semiconductive paste as is well known in the taking of electrocardiograms. A 1.5 volt potential is thus set up through the body and the needle with the needle having a negative potential. It is found that the needle 10 of the aluminum-magnesium alloy can be used as a tap and can remain in position for periods longer than eight hours or more without clogging occurring with blood being drawn at one hour intervals. When this procedure is repeated, using a stainless steel needle, the stainless steel needle will remain unclogged for long periods of time indicating that the negative potential of the needle is useful no matter what the composition of the metal used.

It is believed that the negative potential of the needle repels blood particles which are normally negatively charged and prevents accumulation of blood particles and clotting within and around the shaft 12 of the needle even if it is made of conventional stainless steel or other conductive metals.

The potential applied to the needle may vary considerably; however, it is believed that at least .4 volt is required in order to obtain the results desired.

While specific embodiments of this invention have been shown and described, it should be understood that many variations are possible. For example, the specific metal composition may vary greatly so long as the metal of the walls in contact with the blood forms a coating thereover which imparts an alkaline pH at the very localized area of the wall. Moreover, walls of the metal compositions of this invention can be used in other applications than hypodermic needles. The specific size and configuration of the needle may vary greatly and slotted or perforated needles of known design can be improved by the use of the compositions and method described above. While it is preferred that the hubs of the needles be formed of the same material as the shafts 12, the hubs can be formed of conventional stainless steel or other materials with the shafts 12 welded or force-fitted into the hub. The needles can be used to intermittently introduce medicaments into the blood vessels over prolonged periods of time without withdrawing the needle.

In view of the many modifications possible, this invention is to be limited only by the spirit and scope of the appended claims.

What is claimed is:

1. Means for preventing the formation of blood clots about a surgical opening in body tissue comprising, a foreign element adapted to be inserted and maintained partially within body tissue through a surgical opening therein, a non-organic physiologically non-toxic obturator positioned within and operatively associated with said foreign element and adapted to be at least partially projected into said body tissue, said non-oragnic obturator having means adapted to produce a negative voltage with respect to said body tissue when inserted therein, said non-organic obturator being adapted to react with said body tissue when inserted therein to produce an alkaline corrosion product in the form of a soft gel, said non-organic obturator including a material selected from the group consisting of two elements of ion derivatives thereof in dissimilar amounts.

with one said element or ion derivative thereof being present in a minor amount, being located in the electrochemical series no lower than thallium and being selected from the group consisting of aluminum, magnesium, titanium, lithium, sodium, potassium, rubidium, calcium, cesium, barium, lanthanum, scandium, zirconium, vanadium hafnium, boron, silicon and strontium, said non-organic obturator having an elongated shaft extending through said foreign element with the tip of said obturator projecting into contact with said body tissue.

2. A means as set forth in claim 1 wherein said element in the minor amount comprises magnesium.

3. A means as set forth in claim 2 wherein said other of said two elements comprises aluminum.

4. Means for preventing the formation of blood clots about a surgical opening in body tissue comprising.

a foreign element adapted to be inserted and maintained partially within body tissue through a surgical opening therein, a non-organic physiologically non-toxic obturator positioned within and operatively associated with said foreign element and adapted to be at least partially projected into said body tissue, said non-organic obturator having means adapted to produce a negative voltage with respect to said body tissue when inserted therein, said non-organic obturator being adapted to react with said body tissue when inserted therein to produce an alkaline corrosion product in the form of a soft gel, said non-organic obturator including a material selected from the group consisting of two elements or ion derivatives thereof in dissimilar amounts, with one said element or ion derivative thereof being present in a minor amount, being located in the electrochemical series no lower than thallium and being selected from the group consisting of aluminum, magnesium, titanium, lithium, sodium, potassium, rubidium, calcium, cesium, barium, lanthanum, scandium, zirconium, vanadium, hafnium, boron, silicon and strontium, said non-organic obturator being formed of a plurality of flexible wires with at least one of said wires comprising said one element present in a minor amount.

5. A means as set forth in claim 4 wherein at least two of said flexible wires are present and are formed of dissimilar metals.

6. An instrument adapted to be partially projected into a human body comprising, an obturator formed as an elongated member positioned within and operatively associated with a tubular medical device having one end extending into said body, said obturator having a metal component which is substantially physiologically non-toxic with the tissues of said body and which is selected from the group of elements consisting of aluminum and other elements higher in the electrochemical series, an elongated portion of said obturator extending into said tubular medical device.

7. An instrument as set forth in claim 6 wherein said obturator comprises a plastic matrix and said element is in the form of finely divided particles dispersed throughout said matrix.

8. An instrument as set forth in claim 6 wherein said obturator has an end which extends beyond said tubular medical device.

9. An instrument as set forth in claim 6 wherein said obturator has an end positioned within said tubular medical device adjacent the end of said device within said human body.

10. An obturator for use with a medical device adapted to be partially projected into a human body comprising, an elongated means adapted to be positioned adjacent said device with one end extending into said body, and said means having a finely divided component selected from a group of materials consisting of a metal in metallic free form, metal oxide and metal hydroxide suspended in a plastic means with said means substantially physiologically non-toxic with the tissues of said body and wherein said metal in metallic free form, metal of said oxide and the metal of said hydroxide are selected from a group of elements no lower in the electrochemical series than thallium.

11. A method of minimizing coagulation of blood about a metal medical device partially inserted into a medically formed opening in body tissue comprising, selecting and inserting an obturator comprising a metal higher in the electrochemical series than the metal of said medical device and higher in said series than thallium into the medically formed opening within and electrically insulated from the medical device with ends of the medical device and obturator adjacent and electrically connected through said body tissue.

12. A method of minimizing coagulation of blood about a medical device partially inserted into a medically formed opening in body tissue comprising establishing a negative potential on the portion of said medical device within said opening with respect to the contiguous body tissue, said medical device being a surgical needle and carrying an obturator within it, said obturator comprising a metal higher in the electrochemical series than thallium.

*13. A physiologically non-toxic hypodermic needle for introducing and withdrawing fluids in the body, said needle comprising,*

*a hollow tubular portion adapted to be inserted and maintained partially within a body vessel,*

*said hollow tubular portion being composed entirely of an aluminum-magnesium alloy containing from about 2½% to about 20% magnesium and the balance substantially aluminum, which alloy is non-toxic to the body and which produces a negative charge when in contact with blood to prevent blockage of said hollow tubular portion by preventing buildup of clots within the hollow tubular portion and its vicinity.*

*14. A method of minimizing coagulation of blood in a hollow tubular member inserted into a blood vessel in the body and extending partially out of said body,*

*said method comprising,*

*selecting said member with a surface formed of an aluminum-magnesium alloy containing from about 2½% to about 20% of magnesium and the balance substantially aluminum, which alloy produces a negative charge when in contact with blood,*

*inserting said member partially into the body,*

*maintaining said member partially within said body whereby blockage of said hollow tubular portion is prevented due to said negative charge produced by said material.*

References Cited

The following references, cited by the Examiner, are of record in the patented file of this patent or the original patent.

UNITED STATES PATENTS

| | | | |
|---|---|---|---|
| 722,203 | 3/1903 | Brooke | 128—221 |
| 144,352 | 11/1873 | Nimmo | 128—221 |
| 2,437,697 | 3/1948 | Kalom | 128—221 X |
| 2,836,180 | 5/1958 | Struss, Jr. | 128—214.4 |
| 3,030,953 | 4/1962 | Koehn | 128—214.4 |
| 3,078,850 | 2/1963 | Schein et al. | 128—2.1 X |
| 3,097,646 | 7/1963 | Scislowicz | 128—214.4 |
| 3,204,634 | 9/1965 | Koehn | 128—214.4 |
| 1,891,304 | 12/1932 | Everett | 128—221 X |
| 2,637,316 | 5/1953 | Grez | 128—2.1 R |
| 2,512,569 | 6/1950 | Saffir | 128—221 |
| 2,217,602 | 10/1940 | Smith | 128—221 |
| 3,557,795 | 1/1971 | Hirsch | 128—335.5 |

FOREIGN PATENTS 2,628 Great Britain.

OTHER REFERENCES

Mirkovitch, Cleveland Clinic Quarterly, vol. 30, October 1963, pp. 241–252.

Sawyer et al., Proc. N.A.S., vol. 53, 1965, pp. 294–300.

Sawyer et al., Arch. Surg., vol. 91, November 1965, pp. 735–742.

Chemical Rubber Publishing Co., Handbook of Chemistry and Physics, 43rd ed., 1961-1962, p. 1538.

Ephraim, Inorganic Chemistry, 4th ed., Interscience Publishers, Inc., New York, N.Y., p. 151.

RICHARD A. GAUDET, Primary Examiner

J. C. McGOWAN, Assistant Examiner

U.S. Cl. X.R.

128—214.4, 334

UNITED STATES PATENT OFFICE

CERTIFICATE OF CORRECTION

Patent No. Re. 27,923 Dated Feb. 19, 1974

Inventor(s) Itzhak E. Bentov

It is certified that error appears in the above-identified patent and that said Letters Patent are hereby corrected as shown below:

Column 1; line 7, change "1968" to --1966--
Column 3; line 39, change "form" to --from--
Column 4; line 21, change "21" to --31--
line 41, change "platlets" to --platelets--
Column 7; line 62, change "withdrawn" (second occurrence) to --withdrawal--
Column 8; line 6, change "shat" to --shaft--
Column 9; line 61, change "non-oragnic" to --non-organic--
line 69, change "." to --,--
Column 10; line 12, change "." to --,--

Signed and sealed this 6th day of August 1974.

(SEAL)
Attest:

McCOY M. GIBSON, JR.
Attesting Officer

C. MARSHALL DANN
Commissioner of Patents

USCOMM-DC 60376-P69
☆ U.S. GOVERNMENT PRINTING OFFICE : 1969 O—356-334